US006521791B1

(12) United States Patent
Welp et al.

(10) Patent No.: US 6,521,791 B1
(45) Date of Patent: Feb. 18, 2003

(54) PROCESS FOR REGENERATING A MONOLITH HYDROGENATION CATALYTIC REACTOR

(75) Inventors: Keith Allen Welp, Macungie, PA (US); Anthony Rocco Cartolano, Orefield, PA (US); Frederick Carl Wilhelm, Zionsville, PA (US); William Joseph Mazzafro, Schnecksviile, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/007,202

(22) Filed: Nov. 9, 2001

(51) Int. Cl.$^7$ ............................................. C07C 209/36
(52) U.S. Cl. ....................................... 564/423; 564/420
(58) Field of Search ................................. 564/423, 420

(56) References Cited

U.S. PATENT DOCUMENTS 6,005,143 A    12/1999  Machado et al. ........... 564/423

6,043,394 A    3/2000  Langer et al. .............. 564/423

FOREIGN PATENT DOCUMENTS

WO    9919292    4/1999    ......... C07C/209/36

*Primary Examiner*—Samuel Barts
(74) *Attorney, Agent, or Firm*—Mary E. Bongiorno

(57) ABSTRACT

The invention is a process to regenerate monolith catalytic reactors employed in the liquid phase hydrogenation reactions, particularly those kinds of reactions involving nitroaromatic compounds. The catalytic metals in the monolith catalytic reactor are deactivated by carbonaceous and deactivating byproducts and must be regenerated to extend the catalyst service life and reduce costs. The regeneration process involves two steps: initially passing an oxidizing gaseous mixture through the monolith catalytic reactor at an elevated temperature and for a time sufficient to remove carbonaceous and deactivating byproducts; and then passing a reducing gas though the monolith catalytic reactor previously exposed to the oxidizing gas under conditions for reducing the catalytic metal to its reduced state.

15 Claims, No Drawings

PROCESS FOR REGENERATING A MONOLITH HYDROGENATION CATALYTIC REACTOR

BACKGROUND OF THE INVENTION

Industrial reactions between reactant gases and liquids such as those involving the hydrogenation of unsaturated organic compounds and those having functional groups capable of condensation with hydrogen are often performed by using finely divided powdered slurry catalysts in stirred-tank reactors. These slurry phase reaction systems are inherently problematic in chemical process safety, operability and productivity. The finely divided, powdered catalysts are often pyrophoric and require extensive operator handling during reactor charging and filtration. By the nature of their heat cycles for start-up and shut-down, slurry systems promote co-product formation which can shorten catalyst life and lower yield to the desired product.

An option to the use of finely divided powder catalysts in stirred reactors has been the use of pelleted catalysts in fixed bed reactors. While this reactor technology does eliminate much of the handling and waste problems, a number of engineering challenges have not permitted the application of fixed bed reactor technology to the reaction of gases with liquid organic compounds. Controlling the overall temperature rise and temperature gradients in the reaction process has been one problem. A second problem is that in fixed bed packed reactors there is a significant pressure drop due to the high flow rates required for hydrogenation. A third problem is that liquid-gas distribution is problematic thus often leading to poor conversion and localized concentration gradients.

Monolith catalytic reactors are an alternative to fixed bed reactors and have a number of advantages over conventional fixed bed reactors. These reactors have low pressure drop which allow them to be operated at higher gas and liquid velocities. These higher velocities of gas and liquids promote high mass transfer and mixing and the parallel channel design of a monolith inhibits the coalescence of the gas in the liquid phase.

The use of monolith catalytic reactors has also led to problems in catalytic metal regeneration. Liquid phase hydrogenation of organic compounds can be quite different from gas phase hydrogenation in the types of byproducts, e.g., tars, formed. Penetration of the catalytic surfaces by liquid reactants and solvents may cause these byproducts to become embedded or deposited within the catalytic metal and support. Slurry phase hydrogenation reactions often use solvents to remove deposits followed by reduction of the catalyst to an activated state. However, such treatment may not be not suited for the regeneration of monolith catalytic reactors.

The following patents and articles are illustrative of the prior art as they relate to hydrogenation of aromatic compounds in monolith catalytic reactor.

U.S. Pat. No. 6,005,143 relates to an improvement in a process for hydrogenating a nitroaromatic composition, namely dinitrotoluene, by contacting the dinitrotoluene with hydrogen in a monolith catalytic reactor under liquid phase conditions. Broadly the improvement resides in the continuous, essentially solventless, adiabatic hydrogenation of dinitrotoluene to toluenediamine in a monolith catalytic reactor operating in plug flow.

WO 99/19292 discloses a continuous process for producing aromatic diamines by the fixed bed catalytic hydrogenation of aromatic dinitro and polynitro compounds with hydrogen in the presence of hydrogenated product. Nickel carried on a support, Raney nickel, and palladium on carbon are suggested as catalysts. Regeneration of the catalyst is effected by terminating the feed aromatic dinitro or polynitro compounds while continuing flow of hydrogenation product and hydrogen through the reactor.

U.S. Pat. No. 6,043,394 discloses the fixed bed, gas phase hydrogenation of nitroaromatic amines. Catalytic metals suited for the hydrogenation include palladium carried on a support. Deactivated beds are regenerated with $N_2/O_2$ mixtures at temperatures of from 200 and 400° C., preferably between 250 and 350° C. Preferably, regeneration is begun at $N_2$ contents of between 90 and 99% and O2 contents of from 1–9% with the $O_2$ content being raised in stages to pure air. At the end of regeneration, tenacious carbon residues may optionally be burned off with pure oxygen. Inert carrier gases other than nitrogen, such as for example argon, helium or steam, may also be added to oxygen or air.

BRIEF SUMMARY OF THE INVENTION

The invention relates to an improvement in a process for regenerating monolith catalytic reactors employed in liquid phase hydrogenation reactions, particularly those kinds of reactions involving nitroaromatic compounds. Over time, the catalytic metals in the monolith catalytic reactor become deactivated, because of the deposition of carbonaceous and deactivating byproducts, and the catalytic metals must be regenerated in order to extend the catalyst service life and reduce costs. The regeneration process involves two steps. The first step involves oxidation of the carbonaceous and deactivating byproducts at moderate temperatures and the second step involves reduction of the active catalytic metal species to its activated state.

Significant advantages can be achieved by the practice of this invention and these include:

an ability to extend the service life of a monolith catalytic reactor used in liquid phase hydrogenation reactions;

an ability to minimize downtime of the monolith catalytic reactor caused by catalytic metal deactivation because of simple and efficient regeneration procedures; and, an ability to substantially activate the catalytic metal employed in the monolith catalytic reactor to original activity levels.

DETAILED DESCRIPTION OF THE INVENTION

In the hydrogenation of liquid organic compounds such as unsaturated organic compounds and those having functional groups capable of condensation with hydrogen, particularly nitroaromatic compounds, catalyst activity degrades over time. This decay of activity can be attributed to a number of factors, which include the deposition of non-volatile carbonaceous products, such as, tars and deactivating byproducts, such as cresols, on the catalytic metal surface. In the hydrogenation of dinitrotoluene, for example, tar-like byproducts can be formed by several reactions, including: (a) linking of two or more product toluenediamine molecules, and (b) reactions between a toluenediamine product molecule and dinitrotoluene, or an intermediate product, amino-nitrotoluene.

Essentially two steps are involved in the regeneration process. The first step requires oxidation of contaminant species, e.g., carbonaceous and deactivating byproducts at moderate temperature and the second step requires reduction of active catalytic metal, such as, nickel and palladium.

In the first step, oxidation of the byproducts contaminating the catalytic metals is effected under gas phase conditions by passing an oxidizing gas at an elevated temperature through the monolith catalytic reactor for a time sufficient to effect substantial removal of the carbonaceous products, tars and deactivating byproducts. The oxidizing gas typically is a blend of oxygen in combination with an inert gas. Often, a blend of an oxidizing gas comprised of 1 to 50%, preferably 2 to 15%, oxygen by volume, with a balance of an inert gas is passed into the monolith catalytic reactor. Representative inert gas species include nitrogen, helium, or argon.

Under oxidation conditions, the effluent containing unreacted oxidizing agent, water, contaminants, and $CO_2$ evolved during oxidation of the catalyst are removed. To achieve oxidizing conditions temperatures of from 250–450° C. are used. Higher temperatures may reduce the cycle time required for complete oxidation, but such temperatures also may lead to sintering of the active metal species thereby destroying the catalyst activity.

Flow rates of the oxidizing gas depend on the total open cross-sectional area of the catalyst bed. This is defined as the open cross-sectional area of each monolith cell times the total number of cells available to flow. Flow rates are set to achieve 250–750 cm/sec gas velocities over the catalyst. The gas flow rate should be selected so as to effect the oxidation in practical time. Too low a flow rate results in insufficient oxygen and extends the regeneration cycle. Too high a flow rate increases gas usage without additional benefit, since the regeneration rate is constrained by the oxygen content and temperature of the feed gas. The regeneration process can be monitored by studying the evolution of carbon dioxide. The oxidation step is complete when carbon dioxide concentrations in the exit gas return to background levels.

The second step of the regeneration process involves the reduction of the catalytic metal species in the monolith catalytic reactor to an activated state. A regenerating gas comprised of 0.1 to 10% hydrogen by volume, with the balance being an inert gas, is used to effect reduction of the catalytic species and to substantially return it to its activated state. Reduction temperatures for the second step range from 300 to 450° C. Again these temperatures are sufficient to achieve reasonable cycle times, but do not lead to sintering of the metal and thus loss of activity. Also, feed gas flow rates are set to achieve 250 to 750 cm/sec gas velocities over the catalyst.

In summary, temperature conditions for oxidation must exceed the initiation temperature for destruction of the fouling species. Similarly, the temperatures used for the reduction step must be sufficient to reduce metal oxides and thereby activate the catalyst for use.

Monolith supports for use in a monolith catalytic reactor employed in the process described herein consist of an inorganic porous substrate, a metallic substrate, or a modified substrate, i.e., a monolith support, the support then being coated with a catalytic metal. Often the monoliths are based upon a honeycomb of long narrow capillary channels, circular, square, rectangular or other geometric shape, whereby gas and liquid are co-currently passed through the channels under a laminar flow regime.

The pressure drop within an effective monolith catalytic reactor can range from 2 kPa/m to 200 kPa/m for combined gas/liquid superficial velocities between 0.1 to 2 meters/second for 50% gas holdup in a monolith catalytic reactor having 400 cpi (cells per square inch). Typical dimensions for a honeycomb monolith cell wall spacing range from 0.5 to 5 mm between the plates. Alternatively, the monolith catalytic reactor may have from 100 to 1200, preferably 200 to 600 cpi. Channels may be square, hexagonal, circular, elliptical, etc. in shape.

Catalytic metals suited for reaction obviously depend upon the type of reaction to be effected. For example, hydrogenation of unsaturated organic compounds and those having functional groups capable of condensation with hydrogen utilize catalytic metals which are impregnated or directly coated onto the monolithic substrate, a modified substrate, or a washcoat. The catalytic metals include those Group VIb, Group VIIb, Group VIII, and Group Ib of the periodic table and conventionally used in hydrogenation reactions. Examples of catalytic metal components include cobalt, nickel, palladium, platinum, copper, rhodium, ruthenium, rhenium, iridium and so forth. Often a mixture of metals are employed, one example being a mixture of palladium and nickel.

Catalytic metals are applied to the monolith substrate using a washcoat. The composition of catalytic metals is typically identified as a weight percent within the washcoat itself. The washcoat may be applied in an amount of from 1 to 50% of the total weight of the monolith support. Typical catalyst metal loadings, then, range from 0.1 to 25% by weight and preferably from 1 to 20% by weight of the washcoat. The catalytic metals may be incorporated into the monolith in a manner generally recognized by the art. Incipient wetness from a salt solution of the catalytic metal is one example of a method for incorporating a metal catalytic component on the monolith substrate or modified monolith.

The following examples are intended to illustrate various embodiments of the invention and are not intended to restrict the scope thereof.

GENERAL PROCEDURE

Hydrogenation of Dinitrotoluene In Monolith Catalytic Reactor

Hydrogenation of dinitrotoluene is carried out in a 400 cell per square inch cordierite monolith catalytic reactor washcoated with a high surface area alumina and nominally loaded with 1% Pd and 20% Ni (calculated as a percentage of washcoat loading) as the active metals were prepared and used for the hydrogenation of dinitrotoluene to toluenediamine. The initial activity of the catalyst is approximately 1.7–2.9 mole/$m^3$/sec. and the catalyst shows a weight loss on ignition of less than 1% prior to use. After an extended run, where 81 kg of dinitrotoluene is fed to the reactor, activity declined sharply indicating fouling. The activity just prior to stopping the DNT feed is approximately 0.9 mole/$m^3$/sec. Gravimetric analysis of the catalyst at this point indicates 6–15 weight % loss on ignition (LOI).

EXAMPLE 1

Regeneration of Monolith Catalytic Reactor

Regeneration of the deactivated monolith prepared in accordance with the general procedure involved two sequential steps. In the first step, a blend of 5% by volume of oxygen and the balance nitrogen is fed to the reactor such that gas velocity over the catalyst is 300–400 cm/sec. Temperatures are ramped to 120–150° C. and held for 30 to 90 minutes to remove water from the catalyst surface. Temperatures then are raised to elevate the monolith catalytic reactor to a temperatures between 370 and 425° C. The composition of the effluent is monitored, and the major components detected are carbon dioxide, water, oxygen, and the inert (nitrogen or helium). After from 20 to 30 hours at the higher temperatures, the $CO_2$ concentration in the effluent gas drops to the background level. The system is then cooled under inert gas flow.

After oxidation of the carbonaceous and deactivating byproducts in the previous step, a gas feed of 4% hydrogen by volume in nitrogen at a flow sufficient to achieve 300–400 cm/s gas velocities is passed through the monolith catalytic reactor. The system is heated to 120° C. to evolve adsorbed water then rapidly ramped to 350–420° C. The catalyst is held at this condition for between 2 and 3 hours while the effluent composition is monitored. The effluent during this step contained water, hydrogen and nitrogen as the major components. The system is cooled after the observed water content of the effluent is seen to drop, indicating complete reduction of active metals.

The regenerated monolith catalytic reactor is then returned to service for the hydrogenation of DNT to TDA. The activity of the catalyst for hydrogenation is found to be 1.7–2.1 mole/m$^3$/sec following regeneration. Thus, regeneration returned the catalyst to activities similar to initial values. Catalyst samples following regeneration show 1 weight % LOI, indicating removal of the fouling species.

COMPARATIVE EXAMPLE 2

Regeneration of Monolith Catalytic Reactor Without Oxidation

A deactivated monolith catalytic reactor is generated in accordance with the general procedure. Regeneration is effected in accordance with the general procedure of WO 99/19292. Specifically, dinitrotoluene feed is shut down to the monolith catalytic reactor and hydrogen is passed through the reactor along with hydrogenated byproduct for a time of from 1 to 4 hours. After several unsuccessful regeneration attempts via cessation of dinitrotoluene feed, the reactor is finally shutdown. Catalyst samples show 6–15 weight % LOI after reactor shutdown. Based upon these unsuccessful attempts, this procedure is deemed unacceptable for regeneration of monolith catalytic reactors.

COMPARATIVE EXAMPLE 3

Regeneration of Monolith Catalytic Reactor Using Isopropanol Pretreatment Without Oxidation The procedure of Example 1 is repeated except that the oxidation step is eliminated. More specifically, the monolith is washed with isopropanol for a time of from 30 to 60 minutes. After washing, the reactor is regenerated per the second step of Example 1 involving the reduction of the catalytic metals. The activity of the monolith catalytic reactor upon return to service is deemed unacceptable.

In summary, conditions of catalyst regeneration must be carefully chosen. The process involves two steps. In the first step, conditions must be sufficient to oxidize and remove the fouling species in a reasonable cycle time, thereby minimizing the total regeneration cycle time required. The second step involves reactivation of the metal species by reduction. Conditions for both steps must not negatively affect the catalytic properties. Excessive temperature can lead to sintering of the active metal, therefore reducing active catalyst surface area and subsequent activity. Practical regeneration procedures require moderate to high temperatures. The sintering properties of a catalyst formed by loading two or more metal species onto a high surface area washcoat are typically different than those of any of the individual component species. The interaction between the high surface area support, or washcoat, and the active metal species has a strong impact on both sintering and regeneration temperatures. Thus, the acceptable conditions window is not clear by simple examination of the component species. Similarly, metal interactions can lead to changes in allowable and practical sintering and regeneration conditions, respectively, which are not obvious given the component species.

What is claimed is:

1. In a process for the heterogeneous catalytic reaction of a mixture of a reactant gas and reactant liquid in a monolith catalytic reactor carrying a catalytic metal under conditions of liquid phase reaction for a time sufficient to generate carbonaceous and deactivating byproducts, the improvement for regenerating the catalytic activity of the monolith catalytic reactor and thereby extend the life of the monolith catalytic reactor, which comprises:

initially passing an oxidizing gaseous mixture through the monolith catalytic reactor at an elevated temperature and for a time sufficient to remove carbonaceous and deactivating byproducts; and then, passing a reducing gas though the monolith catalytic reactor previously exposed to the oxidizing gas under conditions for reducing the catalytic metal to its reduced state.

2. The process of claim 1 wherein the monolith catalytic reactor has from 100 to 1200 cells per square inch.

3. The process of claim 2, wherein the catalytic metal is selected from the group consisting of cobalt, nickel, palladium, platinum, copper, rhodium, ruthenium, rhenium, and iridium.

4. The process of claim 3 wherein the reactant liquid is an organic compound selected from the group consisting of a nitroaromatic, a nitrile, unsaturated organic and the reaction products of a ketone or aldehyde with ammonia or a primary or secondary amine.

5. The process of claim 4 wherein the oxidizing gaseous mixture is a gaseous blend comprised of oxygen and an inert gas, said blend having an oxygen content of 1 to 50% by volume.

6. The process of claim 5 wherein the oxygen content in said blend is from 2 to 15% by volume.

7. The process of claim 6 wherein the inert gas in said blend is nitrogen.

8. The process of claim 5 wherein the reducing gas is comprised of a blend of hydrogen and an inert gas, said blend having a hydrogen concentration of from 0.1 to 10% by volume.

9. The process of claim 8 wherein the oxidation is carried out at a temperature from 250 to 450° C.

10. The process of claim 9 wherein the step of reducing the catalytic metal to its reduced state is carried out at a temperature from 300 to 450° C.

11. The process of claim 10 wherein the organic compound is a nitroaromatic compound.

12. The process of claim 11 wherein the nitroaromatic compound is dinitrotoluene.

13. In a process for the heterogeneous catalytic reaction of a mixture of a hydrogen and dinitrotoluene in a monolith catalytic reactor carrying nickel and palladium as catalytic metals under conditions of liquid phase reaction for a time sufficient to generate carbonaceous and deactivating byproducts, the improvement for regenerating the catalytic activity of the monolith catalytic reactor and thereby extending the life of the monolith catalytic reactor, which comprises:

initially passing an oxidizing gaseous mixture through the monolith catalytic reactor at an elevated temperature and for a time sufficient to remove carbonaceous and deactivating byproducts; and then, passing a reducing gas though the monolith catalytic reactor previously exposed to the oxidizing gas under conditions for reducing the catalytic metals to its reduced state.

14. The process of claim 13 wherein the oxidizing gaseous mixture is a blend of oxygen and nitrogen and the oxygen content is from 2 to 15% by volume and the temperature in the oxidation step is from 250 to 450° C.

15. The process of claim 14 wherein the reducing gas is comprised of a blend of hydrogen and an inert gas, said blend having a hydrogen concentration of from 0.1 to 10% by volume, and the temperature for effecting reduction is from 300 to 450° C.

* * * * *